US00PP35708P2

(12) United States Plant Patent
Ammerlaan

(10) Patent No.: US PP35,708 P2
(45) Date of Patent: Mar. 26, 2024

(54) ***GASTERALOE* PLANT NAMED 'OVROCKS10'**

(50) Latin Name: ***Aloe aristata* x *Gasteria carinate*, x *Gasteraloe beguinii***
Varietal Denomination: OVROCKS10

(71) Applicant: Ovata B.V., Bleiswijk (NL)

(72) Inventor: Johannes Hendrikus Adrianus Ammerlaan, Bleiswijk (NL)

( * ) Notice: Subject to any disclaimer, the term of this patent is extended or adjusted under 35 U.S.C. 154(b) by 0 days.

(21) Appl. No.: 18/445,503

(22) Filed: Sep. 5, 2023

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct x *Gasteraloe* plant named 'OVROCKS10' which is characterized by dark green foliage that is moderately to densely covered with very light greyed-green protuberances arranged in highly irregular transverse lines, abaxial foliar protuberances that coalesce into a solid mass distally, foliage that is broadly margined with light greyed-green, and finely dentate margins with very light greyed-green teeth. The new variety has shown to be uniform and stable in the resulting generations from asexual propagation.

2 Drawing Sheets

Latin name of the genus and species: The Latin name of the genus and species of the novel variety disclosed herein is *Aloe aristata* x *Gasteria carinata*, which is synonymous with the nothogenus and species, x *Gasteraloe beguinii.*

Variety denomination: The inventive variety of x *Gasteraloe* disclosed herein has been given the variety denomination 'OVROCKS10'.

BACKGROUND OF THE INVENTION

Parentage: 'OVROCKS10' originated as a naturally occurring, whole-plant mutation of x *Gasteraloe* 'Flow' (not patented). The inventor of 'OVROCKS10' is a commercial ornamental plant producer and regularly discovers mutations of x *Gasteraloe* at his greenhouse operation in Bleiswijk, The Netherlands. For said mutations which seem to exhibit commercial potential, cuttings are taken to produce trial plants which are subsequently grown for evaluation.

Discovered in July of 2016, the variety now called 'OVROCKS10' was noted for its foliage which was densely covered with light greyed-green foliar protuberances, coalescing into a solid mass distally on the abaxial leaf surface, and broad light greyed-green dentate margins. At the time of discovery, cuttings were taken, and the resulting plants were evaluated at the inventor's greenhouse. After further evaluation it was determined that the candidate plant's unique foliage characteristics would prove favorable for commercial marketability. The new plant was given the denomination 'OVROCKS10'.

Asexual Reproduction: The variety now called 'OVROCKS10' was first asexually propagated by stem cuttings in July of 2016 ata greenhouse in Bleiswijk, The Netherlands and has since been vegetatively propagated through four additional generations. Through subsequent generations, the unique features of this cultivar are stable and reproduced true to type.

SUMMARY OF THE INVENTION

The cultivar 'OVROCKS10' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS10'. These characteristics in combination distinguish 'OVROCKS10' as a new and distinct x *Gasteraloe* cultivar:

1. 'OVROCKS10' exhibits narrow ovate to narrow oblong foliage, with a long mucronate tip, growing in a compact basal rosette with secondary rosettes eventually developing at the base of the primary rosette; and
2. 'OVROCKS10' exhibits relatively dark green foliage that is moderately to densely covered with very light greyed-green protuberances and broadly margined light greyed-green; and
3. 'OVROCKS10' exhibits adaxial foliar protuberances are arranged in highly irregular transverse lines across the laminar surface; and
4. 'OVROCKS10' exhibits abaxial foliar protuberances are arranged in highly irregular transverse lines, coalescing into a solid mass distally; and
5. 'OVROCKS10' exhibits prominent finely dentate margins with very light greyed-green teeth, generally appearing as nearly white.

BOTANICAL DESCRIPTION OF THE PLANT

Figure 1:
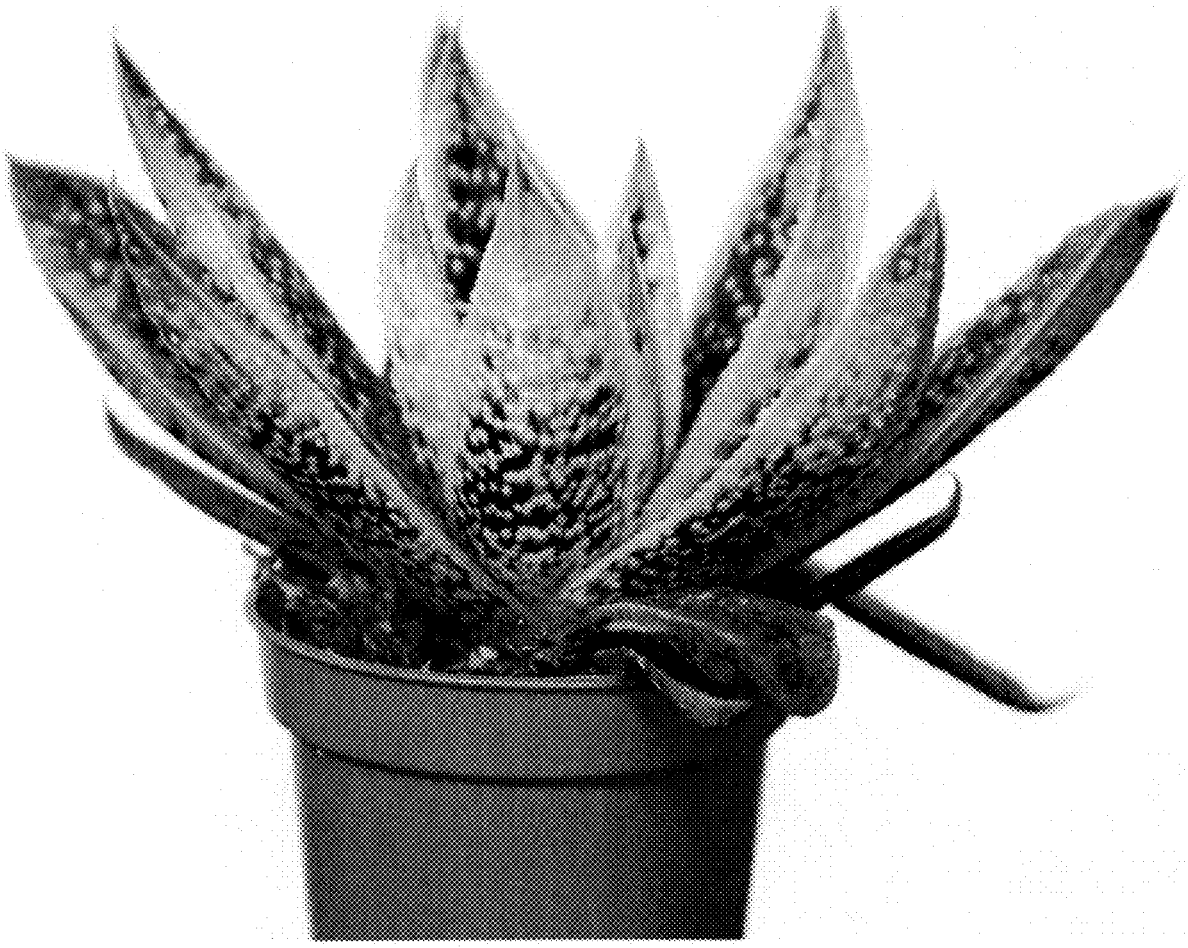
FIG. 1 illustrates, as nearly true as it is reasonably possible to make the same in color photographs of this type, an exemplary plant of 'OVROCKS10' grown in a commercial greenhouse in Bleiswijk, the Netherlands. This plant is approximately 1.5 years old, shown planted in a 5.5 cm container.
Figure 2:
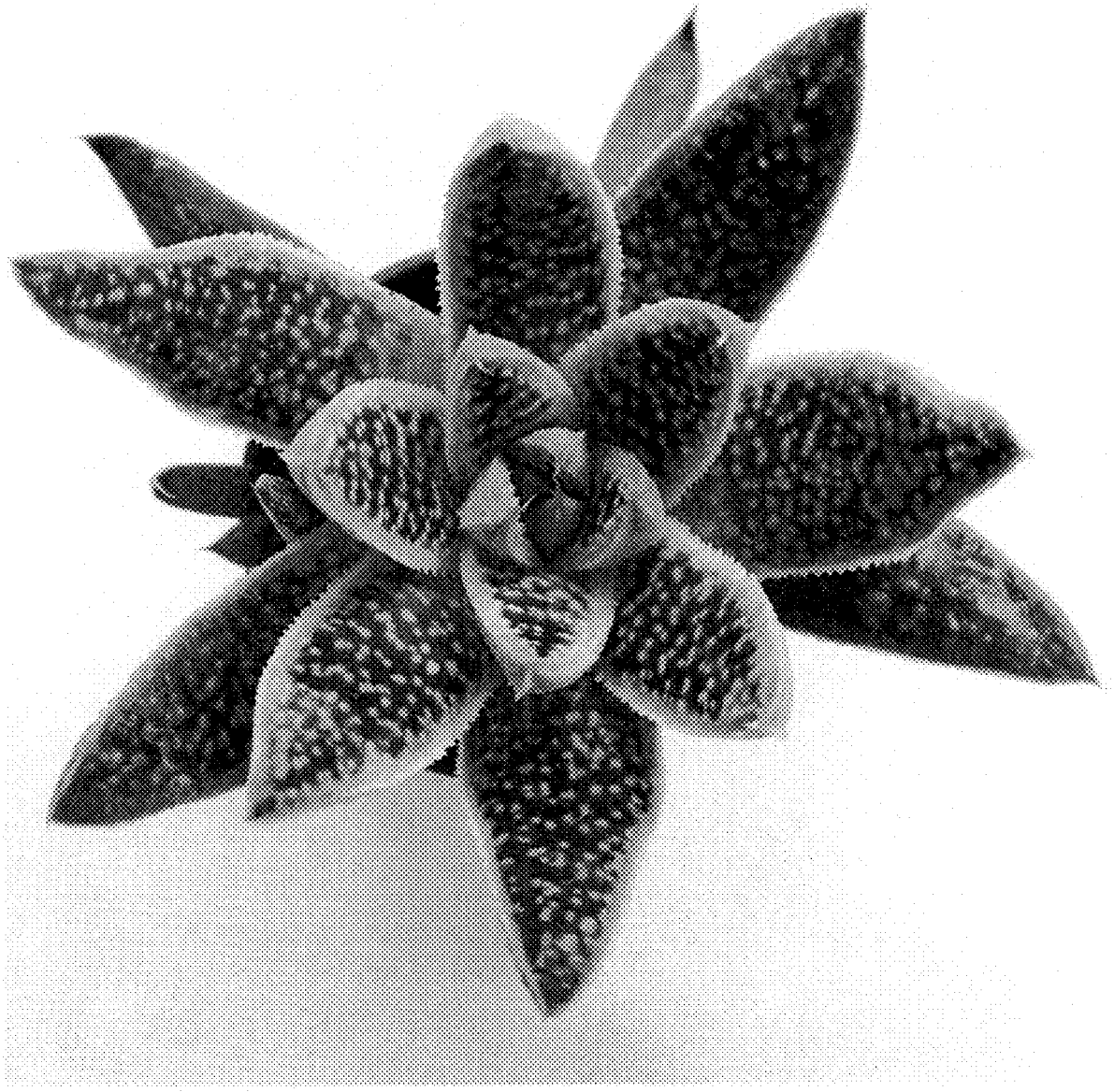
FIG. 2 illustrates, as nearly true as it is reasonably possible to make the same in color photographs of this type, the typical foliage arrangement of 'OVROCKS10'.

The following observations and measurements made in November of 2022 describe averages from a sample set of six specimens of 1.5 years-old 'OVROCKS10' plants grown in 5.5 cm nursery containers at commercial greenhouse in Bleiswijk, the Netherlands. Plants were produced using conventional greenhouse production protocols for x *Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS10' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'OVROCKS10' and a comparison with the parent and closest known comparator is provided below.

Plant description:

*Growth habit.*—Succulent perennial with foliage growing in a compact basal rosette; as plants age, secondary rosettes eventually develop at the base of the primary rosette.

*Plant form.*—Globular to broad obovate.

*Height from soil level to top of foliar plane.*—7.0 cm.

*Plant spread.*—Average of 11.3 cm.

*Plant Vigor.*—Moderately vigorous.

*Propagation.*—Type — Leaf cuttings. Time to initiate rooting — Approximately 5 weeks at an approximate temperature of 21 degrees Celsius. Crop time — Approximately 1 year to produce a marketable plant in a 9 cm container.

*Disease and pest resistance or susceptibility.*—Neither resistance nor susceptibility to typical x *Gasteraloe* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—No stems or branches; leaves arranged in a basal rosette.

Foliage:

*Arrangement.*—Spirally arranged in a basal rosette.

*Division.*—Simple.

*Attachment.*—Sessile.

*Quantity.*—Approximately 20 leaves per rosette.

*Shape.*—Narrow ovate to narrow oblong.

*Dimensions.*—6.8 cm long, 2.1 cm wide, and 0.8 cm thick.

*Aspect.*—Flat to very slightly concave, and carinate. In juvenile foliage, the distal portion of the lamina curls upward.

*Attitude.*—Foliage is held upright at and near the center of the rosettes and becomes progressively more relaxed towards the outer whorls of foliage, at an average angle of 30 degrees from horizontal; lamina is very slightly curled downward with the distal portion at and near the apex being slightly curled upward.

*Apex.*—Apiculate with a long, soft mucronate tip.

*Base.*—Broad cuneate.

*Margin.*—Finely dentate; teeth have an average length of 0.75 cm and are colored greyed-green, nearest to in between RHS 192C and 192D. Margins are not undulated or lobed.

*Pubescence and texture of the adaxial surface.*—Glabrous, smooth, and moderately covered with small, round protuberances that are arranged in highly irregular transverse lines across the laminar surface; protuberances are approximately 0.1 cm in height and diameter, but become progressively larger towards the apex, reaching a size of 0.3 cm in height and diameter.

*Pubescence and texture of the abaxial surface.*—Glabrous, smooth, and moderately to densely covered with small, round protuberances that are arranged in highly irregular transverse lines across the laminar surface; protuberances are approximately 0.1 cm in height and diameter but become progressively larger towards the apex and along the midrib, reaching a size of 0.4 cm in height and diameter. Protuberances coalesce into a solid mass, distally.

*Luster of the adaxial surface.*—Glossy.

*Luster of the abaxial surface.*—Moderately glossy.

*Color.*—Juvenile foliage, adaxial surface — Green, nearest to in between RHS NN137A and 137A, and fading to yellow-green towards the base, nearest to a mixture of RHS 145A and 146D. Protuberances are colored greyed-green, nearest to a mixture of RHS 193A and 193B. Juvenile foliage, abaxial surface — Green, nearest to a mixture of RHS NN137A and NN139A, and fading to yellow-green towards the base, nearest to RHS 145A. Protuberances are colored greyed-green, nearest to a mixture of RHS 193A and 193B. Mature foliage, adaxial surface — Nearest to in between green and yellow-green, RHS 139A and 147A yet slightly darker; fading to yellow-green towards the base, nearest to a mixture of RHS N148B and N148C. Protuberances are colored greyed-green, nearest to a mixture of RHS 191B and 191C. Mature foliage, abaxial surface — Nearest to in between green and yellow-green, RHS NN137A and 147A; fading to yellow-green towards the base, nearest to in between RHS 147D and 148D. Protuberances are colored greyed-green, nearest to RHS 191C.

*Venation*—Pattern — No venation is visible. Color, adaxial surface — No venation is visible. Color, abaxial surface — No venation is visible.

*Petiole.*—No petiole; leaves are sessile.

Inflorescence: No flowering has been observed to date.

Comparisons with the parent plants: Plants of the new cultivar 'OVROCKS10' differ from the seed parent, x *Gasteraloe* 'Flow' (not patented), in the following characteristics described in Table 1 below.

TABLE 1

| Characteristic | 'OVROCKS10' | 'Flow' |
|---|---|---|
| General coloration of the foliage. | Darker green, relative to 'Flow'. | Lighter green, relative to 'OVROCKS10'. |
| Size of foliar protuberances. | Larger than 'Flow'. | Smaller than 'OVROCKS10'. |
| Distribution of foliar protuberances on the abaxial surface. | Arranged in highly irregular transverse lines with protuberances coalescing into a solid mass distally. | Arranged in highly irregular transverse lines; protuberances do not coalesce into a solid mass. |
| Foliar margins. | Finely dentate margins that are prominently and broadly colored light greyed-green, generally appearing as nearly white. | Finely dentate margins that are narrowly colored greyed-orange to light greyed-green. |

Comparison with the closest known comparator: Plants of the new cultivar 'OVROCKS10' differ from the most similar variety known to the inventor, Gasteria 'WT03' (not patented), in the following characteristics described in Table 2 below.

TABLE 2

| Characteristic | 'OVROCKS10' | 'WT03' |
|---|---|---|
| General coloration of the foliage. | Darker green, relative to 'WT03'. | Lighter green, relative to 'OVROCKS10'. |
| Distribution of foliar protuberances on the abaxial surface. | Arranged in highly irregular transverse lines with protuberances coalescing into a solid mass towards and at the apex. | Arranged in highly irregular transverse lines; protuberances do not coalesce into a solid mass. |
| Foliar margins. | Finely dentate margins with light greyed-green teeth, generally appearing as nearly white. Margins are broadly colored with light greyed-green. | Finely dentate margins with teeth colored greyed-orange to light greyed-green. |

That which is claimed is:

1. A new and distinct variety of x *Gasteraloe* plant named 'OVROCKS10', substantially as described and illustrated herein.

* * * * *